(12) United States Patent
Yan et al.

(10) Patent No.: US 10,028,693 B2
(45) Date of Patent: Jul. 24, 2018

(54) VEHICLE STEERING WHEEL

(71) Applicant: BOE TECHNOLOGY GROUP CO., LTD., Beijing (CN)

(72) Inventors: Junwei Yan, Beijing (CN); Jiangbo Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 8 days.

(21) Appl. No.: 14/786,237

(22) PCT Filed: Feb. 16, 2015

(86) PCT No.: PCT/CN2015/073197
§ 371 (c)(1),
(2) Date: Oct. 22, 2015

(87) PCT Pub. No.: WO2016/082359
PCT Pub. Date: Jun. 2, 2016

(65) Prior Publication Data
US 2016/0338632 A1    Nov. 24, 2016

(30) Foreign Application Priority Data
Nov. 24, 2014  (CN) .......................... 2014 1 0682041

(51) Int. Cl.
*A61B 5/18* (2006.01)
*B60Q 9/00* (2006.01)
(Continued)

(52) U.S. Cl.
CPC ............ *A61B 5/18* (2013.01); *A61B 5/14552* (2013.01); *A61B 5/6893* (2013.01); *A61B 5/742* (2013.01);
(Continued)

(58) Field of Classification Search
CPC .......... B60K 28/06; G08B 21/06; A61B 5/18; A61B 5/14552; A61B 5/6893;
(Continued)

(56) References Cited

U.S. PATENT DOCUMENTS 3,731,672 A * 5/1973 McIntosh ................. A61B 5/18
600/372
5,769,085 A * 6/1998 Kawakami ............. A61B 5/024
600/519
(Continued)

FOREIGN PATENT DOCUMENTS

CN     201800755 U     4/2011
CN     203063687 U     7/2013
(Continued)

OTHER PUBLICATIONS

Second Chinese Office Action dated Aug. 10, 2016, for corresponding Chinese Application No. 201410682041.3.
(Continued)

*Primary Examiner* — Peter D Nolan
(74) *Attorney, Agent, or Firm* — Kinney & Lange, P.A.

(57) ABSTRACT

The present invention discloses a vehicle steering wheel, relating to the field of auto part technologies, and solving the problems of being prone to occurrent of traffic accidents and reducing traffic safety when the driver is driving in a fatigue state. In embodiments of the present disclosure, the vehicle steering wheel comprises a wheel rim, at least one oximeter is provided within handheld areas of the wheel rim and connected to a control device connected to an alarm device; and the control device is configured to judge whether or not a driver is in a fatigue driving state according to an oxyhemoglobin saturation value in the body of the driver detected by the oximeter, and to control the alarm device to operate
(Continued)

if judging the driver is in the fatigue driving state. The present invention is mainly applied in vehicles.

11 Claims, 3 Drawing Sheets

(51) Int. Cl.
*A61B 5/1455* (2006.01)
*A61B 5/00* (2006.01)
*B60W 40/08* (2012.01)
*B60W 50/14* (2012.01)
*B62D 1/06* (2006.01)
*B62D 1/04* (2006.01)
*G08B 21/06* (2006.01)

(52) U.S. Cl.
CPC .............. *A61B 5/7405* (2013.01); *B60Q 9/00* (2013.01); *B60W 40/08* (2013.01); *B60W 50/14* (2013.01); *B62D 1/046* (2013.01); *B62D 1/06* (2013.01); *A61B 5/746* (2013.01); *A61B 2503/22* (2013.01); *B60W 2040/0818* (2013.01); *B60W 2040/0827* (2013.01); *B60W 2050/143* (2013.01); *B60W 2050/146* (2013.01); *G08B 21/06* (2013.01)

(58) Field of Classification Search
CPC ....... A61B 5/7405; A61B 5/742; A61B 5/746; A61B 2503/22; B60W 50/14; B60W 2040/0818; B60W 2040/0827; B60W 2050/143; B60W 2050/146
See application file for complete search history.

(56) References Cited

U.S. PATENT DOCUMENTS

| | | | | |
|---|---|---|---|---|
| 6,104,296 | A * | 8/2000 | Yasushi | A61B 5/04085 180/272 |
| 6,822,573 | B2 * | 11/2004 | Basir | G08B 21/06 280/735 |
| 7,397,382 | B2 * | 7/2008 | Ikegami | A61B 5/02416 340/575 |
| 7,894,887 | B2 * | 2/2011 | Yanai | A61B 5/04288 600/509 |
| 8,171,820 | B2 * | 5/2012 | Song | B62D 1/046 340/576 |
| 8,301,108 | B2 * | 10/2012 | Naboulsi | G08B 21/06 340/575 |
| 8,463,352 | B2 * | 6/2013 | Song | B60R 25/04 340/576 |
| 8,725,230 | B2 * | 5/2014 | Lisseman | A61B 5/01 180/272 |
| 8,847,769 | B2 * | 9/2014 | Ershov | A61B 5/0428 340/575 |
| 8,979,761 | B2 * | 3/2015 | Yokoyama | A61B 5/0245 600/484 |
| 9,047,170 | B2 * | 6/2015 | Naboulsi | G08B 21/06 |
| 9,524,034 | B2 * | 12/2016 | Naboulsi | G08B 21/06 |
| 2003/0151516 | A1 * | 8/2003 | Basir | G08B 21/06 340/575 |
| 2004/0133082 | A1 * | 7/2004 | Abraham-Fuchs | A61B 5/6887 600/300 |
| 2004/0209594 | A1 * | 10/2004 | Naboulsi | G08B 21/06 455/404.1 |
| 2006/0038689 | A1 * | 2/2006 | Ikegami | A61B 5/02416 340/575 |
| 2006/0068693 | A1 * | 3/2006 | Kono | A61B 5/14552 454/75 |
| 2007/0123756 | A1 * | 5/2007 | Kitajima | A61B 5/14552 600/300 |
| 2008/0238695 | A1 * | 10/2008 | Yanai | A61B 5/02427 340/576 |
| 2009/0156915 | A1 * | 6/2009 | Cross | A61B 5/0066 600/316 |
| 2009/0227852 | A1 * | 9/2009 | Glaser | A42B 3/0433 600/324 |
| 2010/0137702 | A1 * | 6/2010 | Park | A61B 5/0402 600/393 |
| 2011/0245643 | A1 * | 10/2011 | Lisseman | A61B 5/01 600/372 |
| 2012/0006147 | A1 * | 1/2012 | Sano | A61B 5/0402 74/552 |
| 2012/0078122 | A1 * | 3/2012 | Yokoyama | A61B 5/0245 600/484 |
| 2013/0070043 | A1 | 3/2013 | Geva et al. | |
| 2013/0124038 | A1 * | 5/2013 | Naboulsi | G08B 21/06 701/36 |
| 2013/0231582 | A1 * | 9/2013 | Prasad | A61B 5/746 600/551 |
| 2014/0293053 | A1 * | 10/2014 | Chuang | A61B 5/6893 348/148 |
| 2014/0316227 | A1 * | 10/2014 | Rake | B62D 1/046 600/323 |
| 2015/0057511 | A1 * | 2/2015 | Basu | A61B 5/02433 600/323 |
| 2015/0277579 | A1 * | 10/2015 | Naboulsi | G08B 21/06 345/156 |

FOREIGN PATENT DOCUMENTS

| | | |
|---|---|---|
| CN | 204149972 U | 2/2014 |
| CN | 203902294 U | 10/2014 |
| CN | 104192082 A | 12/2014 |
| CN | 104287721 A | 1/2015 |
| CN | 204196994 U | 3/2015 |
| CN | 204218914 U | 3/2015 |
| GB | 2390460 A | 1/2004 |
| KR | 20060037662 A | 5/2006 |
| KR | 2020080004767 U | 10/2008 |

OTHER PUBLICATIONS

First Chinese Office Action dated Mar. 28, 2016, for corresponding Chinese Application No. 201410682041.3.
International Search Report and Written Opinion from PCT Application Serial No. PCT/CN2015/073197, dated Aug. 19, 2015, 13 pages.
Chinese Rejection Decision dated Dec. 23, 2016, for corresponding Chinese Application No. 201410682041.3.

* cited by examiner

VEHICLE STEERING WHEEL

CROSS-REFERENCE TO RELATED APPLICATION

This application is a Section 371 National Stage Application of International Application No. PCT/CN2015/073197, filed 16 Feb. 2015, entitled "VEHICLE STEERING WHEEL", which has not yet published, and which claims priority to Chinese Application No. 201410682041.3, filed on 24 Nov. 2014, incorporated herein by reference in their entirety.

BACKGROUND OF THE INVENTION

Field of the Invention

The present disclosure generally relates to the field of vehicle part technologies, and particularly, to a vehicle steering wheel.

Description of the Related Art

A vehicle steering wheel is provided, as one of main components of a vehicle steering system, within a driver area of a vehicle, for convenient control of the vehicle.

Generally, a driver sits on a driver's chair and holds the steering wheel by hands (the steering wheel is viewed as a clock dial, a right gesture is in that the left hand holds between 9 and 10 o'clock positions and the right hand holds between 3 and 4 o'clock positions, and such a gesture is more favorable to support the body when a collision occurs), and in a narrow driving space, the driver will fatigue after a long time of driving.

Maladjustments in physiological and psychological functions will occur in the driver when in a fatigue state and will result in lack of concentration, decline in judgment and the like, which is prone to occurrent of traffic accidents and reduces traffic safety.

SUMMARY

Embodiments of the present disclosure provide a vehicle steering wheel, for solving the problems of being prone to occurrent of traffic accidents and reducing traffic safety when the driver is driving in a fatigue state.

In order to achieve the above objects, the following technique solutions are used in the embodiments of the present disclosure:

A vehicle steering wheel, comprises a wheel rim, at least one oximeter is provided within handheld areas of the wheel rim and connected to a control device connected to an alarm device; the control device is configured to judge whether or not a driver is in a fatigue driving state according to an oxyhemoglobin saturation value in the body of the driver detected by the oximeter, and to control the alarm device to operate if judging the driver is in the fatigue driving state.

Preferably, a recess is provided in a rear surface of the wheel rim at a position corresponding to a center area of a side end of the wheel rim; the oximeter is located within the recess, and sealed and fixed in the recess by a cover plate.

Specifically, the recess may comprise two recesses which are symmetrically provided in two side ends of the wheel rim; each of the recesses is an arched recess having two higher side portions and a lower middle portion in a circumference direction of the wheel rim.

Further, the cover plate has a configuration conforming to that of the arched recess and is a transparent plastic plate; the cover plate is adhered and fixedly connected to the wheel rim.

Preferably, four oximeters are provided in each of the recesses and arranged equidistantly in the circumference direction of the wheel rim.

Specifically, the oximeters may be configured so that a probe of each of the oximeters comprises one dual-wavelength light emitting diode and one photodiode; the dual-wavelength light emitting diode is configured to emit light, and the photodiode is configured to receive reflected light after the emitted light is irradiated onto the body.

Preferably, the alarm device comprises a display device connected to the control device; the display device is an indicator or a cue icon.

More preferably, the alarm device further comprises an audio alarm device, the audio alarm device being connected to the control device.

Preferably, the control device is an Electronic Control Unit of a vehicle, and the Electronic Control Unit is provided with a pre-alarming oxyhemoglobin saturation threshold therein.

In the vehicle steering wheel provided according the embodiments of the present disclosure, at least one oximeter is provided within handheld areas of the wheel rim and connected to a control device connected to an alarm device. Thereby, it can be appreciated through analysis that the driver will hold the handheld areas of the wheel rim of the vehicle steering wheel by hands when the driver drives a vehicle; at this times, an oxygen content in fingers of the driver will be detected by the oximeter located within the handheld areas, and an oxyhemoglobin saturation value in the body of the driver is obtained and transmitted to the control device, which judges whether or not the driver is in a fatigue driving state according to the oxyhemoglobin saturation value, and controls the alarm device to operation if judging the driver is in the fatigue driving state, so as to alarm the driver that he/she is being the fatigue driving state, so that the driver can take appropriate measures, for example, pull off and rest, so as to avoid driving in case of lack of concentration and decline in judgment, thereby improving traffic safety.

DETAILED DESCRIPTION OF PREFERRED EMBODIMENTS

The vehicle steering wheel of embodiments of the present disclosure will be described in detail hereinafter with reference to the drawings.

Figure 1:
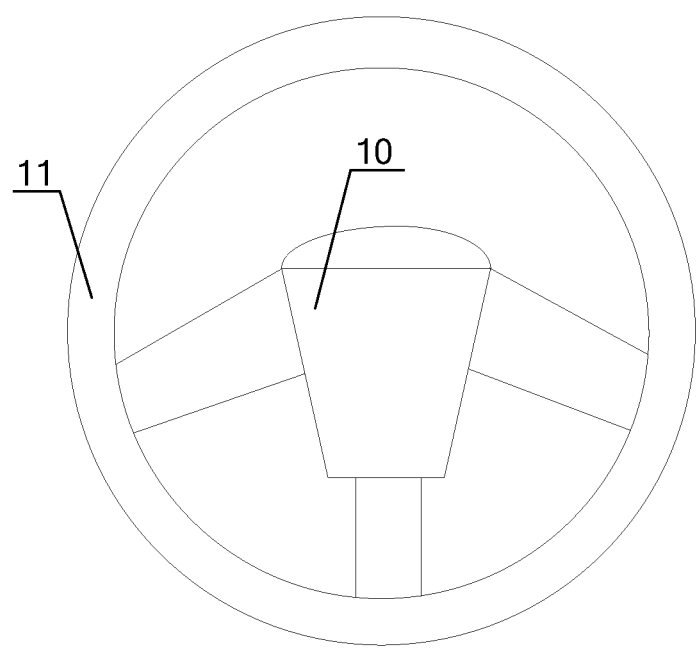
FIG. 1 is a front view of a vehicle steering wheel provided according to an embodiment of the present disclosure.
Figure 2:
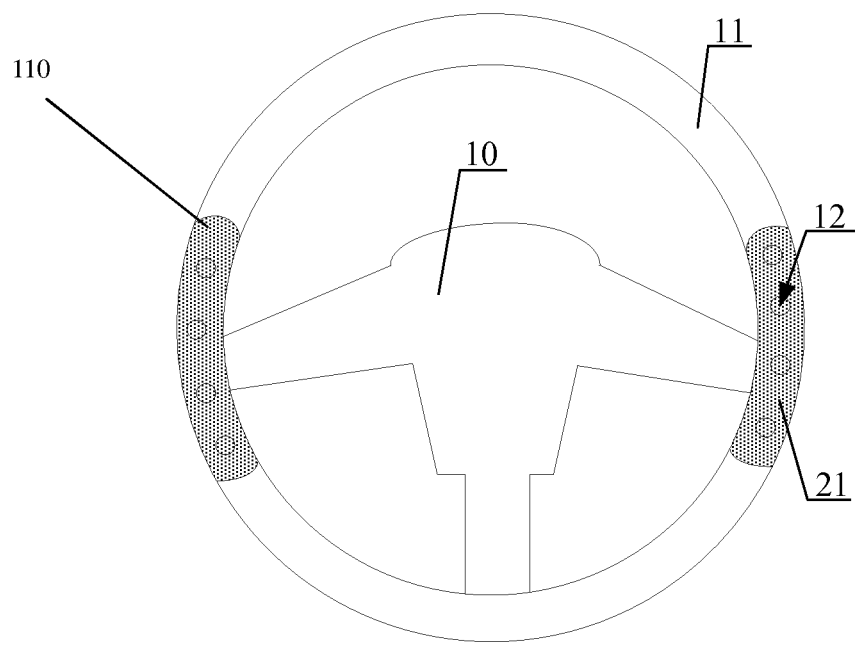
FIG. 2 is a rear view of a vehicle steering wheel provided according to an embodiment of the present disclosure.

Embodiments of the present disclosure provides a vehicle steering wheel, as shown in FIG. 1 and FIG. 2, comprising a wheel rim 11, at least one oximeter 12 is provided within handheld areas A of the wheel rim 11 and connected to a control device (not shown); the control device is further connected to an alarm device (not shown); wherein, the control device is configured to control the alarm device to operate when judging that a driver is in a fatigue driving state according to an oxyhemoglobin saturation value in the body of the driver detected by the oximeter 12.

In the vehicle steering wheel provided according to the embodiments of the present disclosure, at least one oximeter is provided within handheld areas of the wheel rim and connected to a control device connected to an alarm device. Thereby, it can be appreciated through analysis that the driver will hold the handheld areas of the wheel rim of the vehicle steering wheel by hands when the driver drives a vehicle; at this times, an oxygen content in fingers of the driver will be detected by the oximeter located within the handheld areas, and an oxyhemoglobin saturation value in the body of the driver is obtained and transmitted to the control device, which judges whether or not the driver is in a fatigue driving state according to the oxyhemoglobin saturation value, and controls the alarm device to operate if judging the driver is in the fatigue driving state, so as to alarm the driver that he/she is being the fatigue driving state, so that the driver can take appropriate measures, for example, pull off and rest, so as to avoid driving in case of lack of concentration and decline in judgment, thereby improving traffic safety.

Here, it should be noted that it is known, according to medical common knowledge, that fatigue is closely associated with energy and metabolism of macroergic compounds. In a normal case, energy required by main organs of human body is generated through oxidation reaction of substances such as protein, sugar, fat and the like; if energy stored in the human body is consumed soon and can not be complemented timely, people will feel tired or fatigued, thus occurrence of fatigue is closely associated with lack of oxygen in organs.

According to the above principle, by measuring oxyhemoglobin saturation in organs, it can be evaluated whether or not normal oxygen content can be maintained for organs and thereby it can be judged whether or not the body is in a fatigue state.

Further, the handheld areas of the wheel rim of the vehicle steering wheel comprise the whole surface of the wheel rim 11. Among others, during actual driving, although a driver may not keep the right gesture to drive the vehicle according to his/her driving habits and/or after a long driving time, the driver normally keep the right gesture for driving and convenient control (in contrast, a case where both hands of the driver do not keep the right gesture may be neglected). Thus, the handheld areas of the wheel rim in the embodiments of the present disclosure preferably comprise areas where hands cover when the driver drives the vehicle in the right gesture, that is, at least comprise an area between 9 and 10 o'clock positions which is held by the left hand, and an area between 3 and 4 o'clock positions which is held by the right hand.

In addition, the vehicle steering wheel further comprises spokes 10 provided on the wheel rim 11, as shown in FIG. 1.

The above handheld areas may be specifically arranged so that a recess is provided in a rear surface of the wheel rim 11 at a position corresponding to a center area of a side end of the wheel rim, that is, when viewing the vehicle steering wheel as a clock dial, the recess is provided between 8 and 10 o'clock positions and/or between 2 and 4 o'clock positions, and thereby ensuring that the oximeter 12 located within the recess can measure the oxyhemoglobin saturation in the body of the driver. That is, when one hand of the driver holds the wheel rim 11 in the right gesture, the oximeter 12 can obtain the oxyhemoglobin saturation value in the body of the driver by measuring oxygen content in fingers of the driver. In an example, in FIG. 2, the oximeter 12 is sealed and fixed in the recess by a cover plate 21, which may be fixedly connected to the wheel rim 11 by adhesive, or in other ways, such as snap engagement or the like.

In FIG. 2, the area where the oximeter 12 is arranged is an area where the driver typically holds, and of course, the oximeter 12 may be arranged at other positions on the wheel rim 11.

In one example, the oximeter 12 is usually a pulsed oximeter comprising a probe, and during actual assembly, the probe of the oximeter 12 may be embedded in the wheel rim 11, for convenient detection. Specifically, the probe of the oximeter 12 may comprises one dual-wavelength light emitting diode and one photodiode. When the driver drive the vehicle, the oximeter 12 is enabled to detect the oxygen content in the body of the driver; of course, it is also possible that a time parameter (a time when the driver is prone to be tried or fatigued after continuous driving) is set to control the oximeter 12 to operate after the driver has driven over a time period.

The dual-wavelength light emitting diode operates and emits initial light of two wavelengths, which transmits through the cover plate 21 and irradiates fingers of the driver, which absorb some of the initial light and reflect the initial light, so that the reflected light again passes through cover plate 21 and is absorbed by the photodiode. As such, the oxyhemoglobin saturation value in the body of the driver can be obtained by measuring a change in absorptance of the transmitted light caused by finger tips of the driver during pulsation of capillary vessels.

Preferably, the probe of the oximeter 12 utilizes a dual-wavelength light emitting diode so that absorptances of light of various wavelengths by drivers can be measured in order to improve measurement accuracy. Of course, a single-wavelength light emitting diode (a plurality of different single-wavelength light emitting diodes may be provided) or a multi-wavelength (more than two wavelengths) light emitting diode may be also possible.

It can be understood from the above process of measuring the oxyhemoglobin saturation value in the body of the driver, that it is required to receive light reflected by the fingers of the driver finger, thus rationality in measurement can not be ensured (due to poorer receipt of the emitted light) if the probe of the oximeter 12 is placed in direct contact with the fingers, while arrangement of the recess and the cover plate 21 can ensure the measurement is performed normally. In this case, both the initial light and the reflected light will transmit in the cover plate 21, thus in order to ensure that transmission of light will not be affected, for example, blocked or absorbed, by the cover plate 21, the cover plate 21 may be provided as a transparent plastic plate, preferably is made of materials such as polycarbonate and the like. During actual manufacturing, the cover plate 21 has a configuration conforming to that of the recess, thereby ensuring appearance design quality of the whole of the wheel rim 11.

Fully considering actual driving conditions of the driver, as shown in FIG. 1 to FIG. 2, the wheel rim 11 may be provided with two recesses 110, which are the same in structure and size, and which are symmetrically provided in two side ends of the wheel rim 11 so that one of the recesses is located between 8 and 10 o'clock position, while the other is located between 2 and 4 o'clock positions, that is, the two recesses cover areas where the driver holds the steering wheel in the right gesture. Thereby, measurement of the oxyhemoglobin saturation in the body of the driver can be implemented as long as one hand of the driver holds the wheel rim in a right way.

In one example, the recess may be an arched recess, of which two side portions are higher and a middle portion is lower in a circumference direction of the wheel rim 11. Thus, a surface of the cover plate 21 facing the recess is formed into a convex surface to concentrate the reflected light so that the oximeter 12 has a good receipt of light.

Also, in order to facilitate measurement of the oxyhemoglobin saturation value in the body of the driver, four oximeters 12 may provided in each recess and the specific number of the oximeters may be determined as required. In one example, the four oximeters 12 are arranged equidistantly in the circumference direction of the wheel rim 12, that is, in a direction which is consistent with a direction where the fingers are arranged when the driver holds the wheel rim 11, thereby ensuring a multi-orientation and convenient measurement.

In one example, the control device of the vehicle steering wheel is an Electronic Control Unit (ECU) of the vehicle, that is, the oximeter 12 is electrically connected to the ECU so that the oxyhemoglobin saturation value in the body of the driver measured by the oximeter 12 is communicated to and judged by the ECU. Specifically, the ECU may be provided with a pre-alarming oxyhemoglobin saturation threshold therein, thereby the measured oxyhemoglobin saturation value in the body of the driver can be compared with the threshold, and when the measurement is larger than the threshold, it is judged by the ECU that the driver is being in fatigue driving, and a warning is provided by the alarm device to remind the driver to take corresponding measures.

When four oximeters 12 are arranged in the recess, four measured oxyhemoglobin saturation values may be averaged in the ECU to obtain an average value, which is compared with the threshold, thereby improving measurement accuracy.

When it is judged by the ECU that the driver is being in fatigue driving, a control signal is outputted by the ECU to the alarm device, for warning operation. In one example, the alarm device may comprise a display device connected to the ECU, for example, an indicator or a cue icon; when the alarm device comprise a cue icon, a driving computer screen may be used as the display device, thereby the ECU controls the display device to constantly light or to wink at a frequency so as to warn the driver. Of course, the alarm device may also comprise an audio alarm device connected to the ECU, so that the ECU controls the audio alarm device to alarm, specifically, several times of hoots or the like, while controlling the display device.

Figure 3:
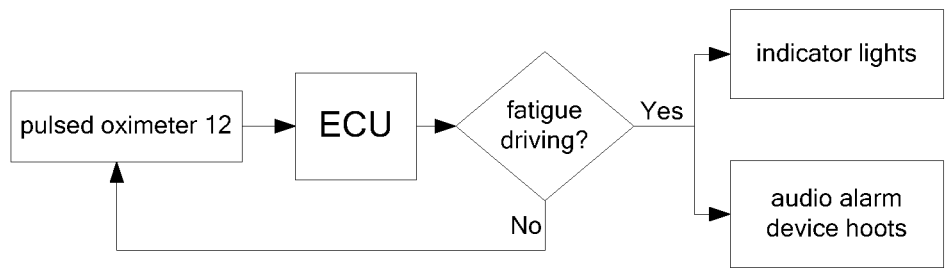
FIG. 3 is a flow chart showing operations of alarming fatigue driving to the driver in a vehicle steering wheel provided according to an embodiment of the present disclosure.

Specifically, a warning flow is shown in FIG. 3 when it is judged that the driver is in fatigue driving. The oxyhemoglobin saturation value in the body of the driver is measured by the oximeter 12 (pulsed oximeter 12), communicated to the ECU and compared with the preset threshold in the ECU for judgment, and when the measurement is larger than the threshold, it is judged that the driver is in fatigue driving, and the display device is controlled to operate (the indicator lights) and audio alarm device hoots.

It is noted in the description of the present disclosure that, orientations or positional relationships indicated by terms "center", "upper", "lower", "front", "rear", "left", "right", "upright", "horizontal", "top", "bottom", "inner", "outer" and the like are based on those shown in the drawings, and these terms are only intended to facilitate and simplify the description of the present disclosure, rather than indicating or implying the mentioned devices or elements must have particular orientations, be configured and operated in particular orientations, and thus should not be understood as being limitative to the present invention.

Terms "first", "second" are merely used for purpose of description, and should not be understood as indicating or implying relative importance or impliedly designating numbers of the mentioned technical features. Thus, a feature defined by "first", "second" may express or imply that one or more the features are included. In the description of the present disclosure, "a plurality of" means two or more, unless otherwise specified.

It should be noted in the description of the present disclosure that, unless otherwise specified or defined, terms "mounting", "coupling", "connection" should be understood in broad sense, for example, may be a fixed connection, or may also be a detachable connection or integrated connection; may be a mechanical connection or an electrical connection; may be a direct connection, or an indirect connection via a intermedium; may be internal communication between two elements. For those skilled in the art, meanings of the above terms in the present disclosure may be understood according to specific conditions.

In the description, specific features, structures, materials or characteristics may be combined in suitable ways in one or more random embodiments or examples.

The above described contents are only preferred embodiments of the present disclosure, but the scopes of the present disclosure are not limited to those, and changes or modifications which are obviously made by those skilled in the art in the disclosure should fall within the scope of the present invention. Thus, the scopes of the present invention are defined in the claims.

What is claimed is:

1. A vehicle steering wheel comprising:
   a wheel rim; and
   at least one oximeter provided within handheld areas of the wheel rim, located in the rear surface of the wheel rim and connected to a control device connected to an alarm device;
   wherein the control device is configured to judge whether or not a driver is in a fatigue driving state according to an oxyhemoglobin saturation value in a body of the driver detected by the oximeter, and to control the alarm device to operate if judging the driver is in the fatigue driving state,
   wherein a recess is provided in the rear surface of the wheel rim, and the oximeter is located within the recess, and sealed and fixed in the recess by a cover plate so as to avoid a finger of the driver from being in direct contact with the oximeter; and
   wherein the recess is an arched recess having two higher side portions and a lower middle portion in a circumference direction of the wheel rim, and the cover plate has a configuration conforming to that of the arched recess.

2. The vehicle steering wheel according to claim 1, wherein the recess is provided at a position of the rear surface corresponding to a center area of a side end of the wheel rim.

3. The vehicle steering wheel according to claim 2, wherein the recess comprises two recesses which are symmetrically provided in two side ends of the wheel rim.

4. The vehicle steering wheel according to claim 3, wherein the cover plate is a transparent plastic plate; and the cover plate is adhered and fixedly connected to the wheel rim.

5. The vehicle steering wheel according to claim 4, wherein four oximeters are provided in each of the recesses and arranged equidistantly in the circumference direction of the wheel rim.

6. The vehicle steering wheel according to claim 3, wherein four oximeters are provided in each of the recesses and arranged equidistantly in the circumference direction of the wheel rim.

7. The vehicle steering wheel according to claim 6, wherein a probe of each of the oximeters comprises a dual-wavelength light emitting diode and a photodiode; wherein the dual-wavelength light emitting diode is configured to emit light, and the photodiode is configured to receive reflected light after the emitted light is irradiated onto the body.

8. The vehicle steering wheel according to claim 7, wherein the probe of each of the oximeters is provided with only one dual-wavelength light emitting diode and one photodiode.

9. The vehicle steering wheel according to claim 1, wherein the alarm device comprises a display device connected to the control device; and the display device is an indicator or a cue icon.

10. The vehicle steering wheel according to claim 9, wherein the alarm device further comprises:
   an audio alarm device, the audio alarm device being connected to the control device.

11. The vehicle steering wheel according to claim 10, wherein the control device is an Electronic Control Unit of a vehicle, and the Electronic Control Unit is provided with a pre-alarming oxyhemoglobin saturation threshold therein.

* * * * *